US00PP18987P2

(12) United States Plant Patent
Sheehan

(10) Patent No.: US PP18,987 P2
(45) Date of Patent: Jun. 24, 2008

(54) GRAPEVINE ('SHEEGENE-7)'

(50) Latin Name: *Vitis vinifera*
Varietal Denomination: (Sheegene-7)

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 11/708,797

(22) Filed: Feb. 20, 2007

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Baker Manock & Jensen, PC; Eric C. Cole

(57) ABSTRACT

A new and distinct variety characterized by medium to large, green-colored seedless grapes that ripen in late June, approximately two weeks earlier than does the Perlette Seedless Grape (unpatented), when grown in the San Joaquin Valley of Central California. The grapes of this new variety are produced on strong stems and are well adapted to commercial handling.

1 Drawing Sheet

Latin name of the genius and species of the plant claimed: The claimed plant relates to a new and distinct variety of *Vitis vinifera* to be known as 'Sheegene-7'.

Variety denomination

This invention relates to a new discovery and asexual propagation of a new variety of *Vitis vinifera*. The new variety was first hybridized by Timothy P. Sheehan of Porterville, Calif. in 2000. The pollen parent is 'Brickeys Best' (unpatented) and the seed parent is 'Red Globe' (U.S. Plant Pat. No. 4,787); the new variety first flowed in 2003. The new variety was asexually propagated in the dormant season of 2003, grafted on 'Harmony', virus-free rootstock near Fowler, Calif. Four vines were planted at that time in a variety block of *Vitis vinifera* located near Fowler, Calif., in the San Joaquin Valley of Central California. The new variety closely resembles 'Perlette Seedless' (unpatented) but the grapes are larger and mature approximately two weeks earlier. The new variety has been shown to maintain its distinguishing characteristics through asexual propagation.

BACKGROUND OF THE INVENTION

The present invention relates to a new and distinct variety of grape which will hereinafter be denominated as 'Sheegene-7' and more particularly as a grapevine which produces a medium to large, green-colored seedless grape, which is mature for commercial harvesting and shipping during the fourth week of June in the San Joaquin Valley of Central California. The new invention most nearly resembles 'Perlette Seedless' (unpatented) but it produces a larger grape that matures approximately two weeks earlier.

SUMMARY OF THE INVENTION

The 'Sheegene-7' grapevine is characterized by producing a medium to large, green-colored seedless grape that is mature for harvesting and shipment during the last week of June in the San Joaquin Valley of Central California. The new variety can be compared to the 'Thompson Seedless' (unpatented)) but the grapes mature about two weeks earlier, among other distinguishing characteristics.

BRIEF DESCRIPTION OF THE DRAWING

The accompanying drawing is a color photograph displaying smaller leaves, tendrils and a terminal, a grape cluster showing the shape of a mature cluster, along side is a secondary small cluster and leaf and stem, below that is another small immature cluster and to the left are four grapes cut in half showing color of flesh and shape of the berry. On the bottom of the drawing is a short section of a mature branch and droppping nodes.

DETAILED BOTANICAL DESCRIPTION

Referring more to the horticultural description of the new and distinct variety of grapevine, the following description has been observed under the ecological conditions prevailing at the origin vineyard which is located east of Fowler, Calif., in the San Joaquin Valley of Central California.

All major color designations are by reference to the Dictionary of Color by Maerz and Paul, First Edition, published in 1930. Common color names are also used in several instances.

Vine:

*Size.*—Very large for four year old vine.
*Vigor.*—Very good.
*Chilling requirements.*—Normal for grapes in the San Joaquin Valley of Central California.
*Figure.*—Regular with cordons extending out forming a T-shape figure.
*Productive capacity.*—Very good.
*Regularity of bearing.*—Regular.

Trunk:

*Size.*—Medium; 19.05 cm (7.5 inches) in circumference, 12 inches above graft.
*Surface texture.*—Rough, shaggy.
*Mature canes.*—Color: P1.12 J6 Honey Middle Stone.
*Nodes.*—Four nodes on canes, 12 inches (30.5 cm) in length.
*Length between nodes.*—8.89 to 11.43 mm (3 to 4 inches).
*Lenticel.*—Numbers: None.

*Lenticel.*—Size: None.
*Tendrils.*—Numbers: One at nodes.
*Tendrils.*—Size: Variable; 7.62 to 8.25 cm (3 to 3 inches).
*Tendrils form.*—Furcate.
*Tendrils.*—Texture: Firm to slight woody.
*Bud shape.*—Slightly triangular (convex).
*Buds size.*—6.35 to 7.62 mm ( to 5/16 inches).
*Bud fruitfulness.*—Very good.

Branches:
*Size.*—Medium; 7.62 cm (3 inches) in circumference.
*Surface texture.*—Slightly rough.
*Color.*—One Year or Older Wood: P1.6 L6 Chianti Antique Ruby.
*Surface texture.*—Immature Growth: Smooth.
*Lenticels.*—Number: 0.

Leaves:
*Size.*—Medium.
*Density.*—Dense.
*Average length.*—Mature Leaves: 10.80 to 12.70 cm (4.25 to 5.0 inches).
*Average width.*—Mature Leaves: 10.80 to 12.70 cm (4.25 to 5.0 inches).
*Form.*—Pentagonal.
*Texture.*—Upper Surface: Smooth.
*Color.*—Upwardly Disposed Surface: P1.23 J8 Mt. Vernon green.
*Color.*—Downwardly Disposed Surface: P1.22 L7 Art green.
*Color.*—Leaf Vein: P1.20 K6 — Piquant green.
*Marginal form.*—Slightly undulate.
*Leaf vein.*—Thickness: 2 mm (0.079 inches).
*Petiole size.*—Large.
*Petiole length.*—6.99 to 15.24 cm (2 to 6 inches).
*Petiole color.*—P1.20 K6 Piquant green.
*Petiole sinus form.*—Upside down U-shape.
*Stem glands.*—None.
*Stipules.*—3 to 5 (0.12 to 0.20 inches).
*Lobes.*—Average: Four.
*Tooth size.*—15 mm (0.625 inches) in length; 15 mm (0.625 inches) in width.
*Tooth.*—Number: Three between lobes.
*Teeth.*—Shape: Convex.

Fruit:
*Solids.*—17.9° Brix.
*Acid.*—0.53.
*Sugar/acid ratio.*—33.7.
*Juice pH.*—3.67.
*Seeds.*—None.
*Capstem pedicel.*—8 to 10 mm (0.31 to 0.39 inches).
*Berry weight.*—Approximately 3.34 grams.
*Juice color.*—P1.4 I9 Marsh Rose.
*Cluster.*—Size: Medium to large.
*Cluster.*—Average Length: 21 cm (8.27 inches).
*Cluster.*—Average diameter: 15 cm (5.9 inches).
*Cluster.*—Weight: 20.02 oz (567 grams).
*Compact.*—Compact.
*Cluster form.*—Conical.
*Stems.*—7.62 to 8.89 cm (3 to 3 inches).
*Berry size.*—Medium.
*Berry form.*—Ovate.
*Berry numbers.*—Approximately 170 per bunch.
*Berry size.*—Average Dimension Along Longitudinal Axis: 18 mm (0.71 inches).
*Berry size.*—Average Dimensions Along Transverse Axis: 19 to 21 mm (0.75 to 0.84 inches).

Skin:
*Skin thickness.*—Medium.
*Texture.*—Semi tough.
*Tendency to crack.*—None.
*Blush color.*—None.
*Ground color.*—P1.20 C7 Surf. gr.
*Pulp.*—Clear.
*Lenticels.*—None.

Flesh:
*Flesh color.*—Clear to P1.20 J5 Absinthe gr.
*Juice production.*—Moderate.
*Flavor.*—Good.
*Aroma.*—Very mild.
*Texture.*—Medium firm.
*Ripening.*—Even.
*Eating quality.*—Very good.
*Use.*—Fresh market.
*Keeping quality.*—Good.
*Resistance to disease.*—Unknown.
*Harvesting.*—Late June.
*Shipping and handling qualities.*—Very good.

Having thus described and illustrated our new variety of grapevine, we claim:

1. A new variety of grapevine to be known as Sheegene-7 and parts thereof, substantially as illustrated and described, characterized principally by its production of medium to large, green-colored seedless grapes, that mature approximately two weeks earlier in the season of ripening than does the Perlette Seedless (unpatented) which is resembles.

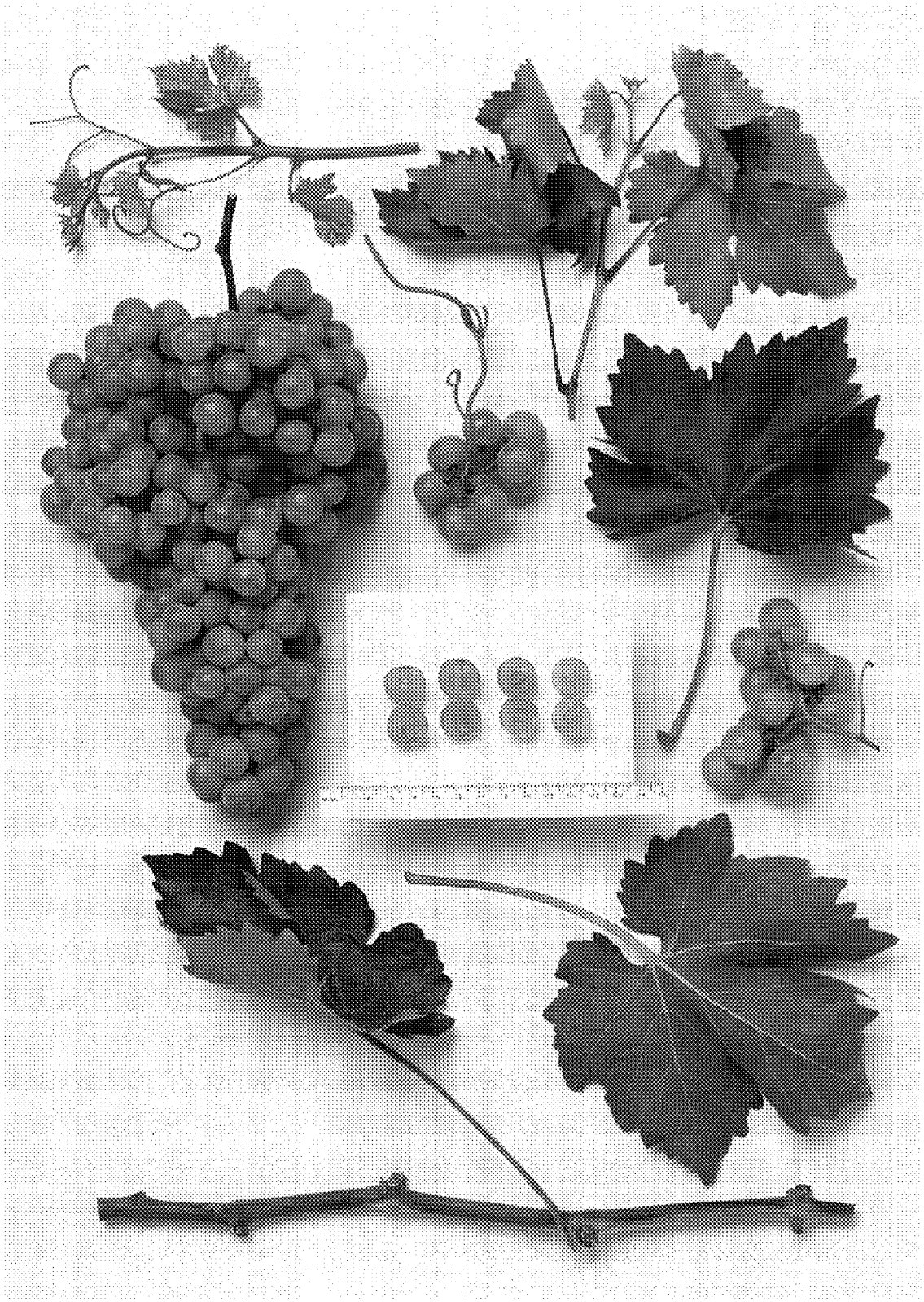

* * * * *